(12) United States Patent
Cargill et al.

(10) Patent No.: US 6,171,555 B1
(45) Date of Patent: Jan. 9, 2001

(54) REACTION BLOCK DOCKING STATION

(75) Inventors: John Cargill, San Diego; Romaine R. Maiefski, Oceanside, both of CA (US)

(73) Assignee: Ontogen Corporation, Carlsbad, CA (US)

( * ) Notice: Under 35 U.S.C. 154(b), the term of this patent shall be extended for 0 days.

(21) Appl. No.: 09/036,252

(22) Filed: Mar. 6, 1998

Related U.S. Application Data

(60) Continuation-in-part of application No. 08/718,106, filed on Sep. 18, 1996, now abandoned, which is a division of application No. 08/422,869, filed on Apr. 17, 1995, now Pat. No. 5,609,826.

(51) Int. Cl.[7] .................................. B01L 9/00; B01L 9/06
(52) U.S. Cl. .............................. 422/104; 422/63; 422/99
(58) Field of Search .................. 422/19, 102, 63, 422/65, 68, 104; 366/110, 111

(56) References Cited

U.S. PATENT DOCUMENTS

| | | | |
|---|---|---|---|
| 3,645,690 | * 2/1972 | Rochte et al. | 436/48 |
| 3,944,188 | 3/1976 | Parker et al. | 366/110 |
| 3,985,508 | * 10/1976 | Williams | 422/65 |
| 4,054,151 | 10/1977 | Parker et al. | 137/110 |
| 4,087,248 | 5/1978 | Miles | 422/63 |
| 4,154,795 | 5/1979 | Thorne | 422/99 |
| 4,304,865 | 12/1981 | O'Brien et al. | 435/240 |
| 4,319,841 | 3/1982 | Suovaniemi et al. | 356/244 |
| 4,483,964 | 11/1984 | Urdea et al. | 525/54.11 |
| 4,517,338 | 5/1985 | Urdea et al. | 525/54.11 |
| 4,659,222 | 4/1987 | Ekholm | 356/244 |
| 4,701,304 | * 10/1987 | Horn et al. | 422/62 |
| 4,746,490 | 5/1988 | Saneii | 422/62 |
| 4,797,259 | 1/1989 | Matkovich et al. | 422/101 |
| 4,830,832 | 5/1989 | Arpagaus et al. | 422/64 |
| 4,931,256 | 6/1990 | Mack et al. | 422/65 |
| 4,931,402 | 6/1990 | Abplanalp | 435/291 |
| 4,948,442 | 8/1990 | Manns | 156/73.1 |
| 4,948,564 | 8/1990 | Root et al. | 422/101 |
| 4,952,518 | 8/1990 | Johnson et al. | 436/518 |
| 4,970,165 | 11/1990 | Uhrin | 435/287 |
| 5,039,493 | 8/1991 | Oprandy | 422/101 |
| 5,048,957 | 9/1991 | Berthold et al. | 356/246 |
| 5,075,079 | * 12/1991 | Kerr et al. | 422/64 |
| 5,108,704 | 4/1992 | Bowers et al. | 422/70 |
| 5,114,681 | 5/1992 | Bertoncini et al. | 422/111 |
| 5,122,342 | 6/1992 | McCulloch et al. | 422/65 |
| 5,190,666 | * 3/1993 | Bisconte | 210/744 |
| 5,206,171 | 4/1993 | Dillon et al. | 435/293 |
| 5,219,528 | 6/1993 | Clark | 422/101 |
| 5,240,680 | 8/1993 | Zuckermann et al. | 422/67 |
| 5,252,296 | 10/1993 | Zuckermann et al. | 422/116 |
| 5,260,028 | 11/1993 | Astle | 422/81 |
| 5,260,872 | 11/1993 | Copeland et al. | 364/413 |
| 5,283,039 | 2/1994 | Aysta | 422/104 |
| 5,306,420 | 4/1994 | Bisconte | 210/143 |
| 5,306,510 | 4/1994 | Meltzer | 422/65 |
| 5,324,483 | 6/1994 | Cody et al. | 422/131 |
| 5,342,581 | 8/1994 | Sanadi | 422/101 |
| 5,350,564 | * 9/1994 | Mazza et al. | 422/63 |
| 5,375,282 | 12/1994 | Dausch et al. | 8/159 |
| 5,443,791 | 8/1995 | Cathcart et al. | 422/65 |
| 5,512,247 | 4/1996 | Bonacina et al. | 422/67 |
| 5,525,300 | 6/1996 | Danssaert et al. | 422/99 |

FOREIGN PATENT DOCUMENTS

| | | |
|---|---|---|
| WO 93/12427 | 6/1993 | (WO) . |
| WO 94/11388 | 5/1994 | (WO) . |
| 96/33010 | * 10/1996 | (WO) . |

OTHER PUBLICATIONS

DeWitt, S.H., et al.; "Diversomers": An approach to non-peptide, nonoligomeric chemical diversity; Proc. Natl. Acad. Sci. USA, vol. 90, pp. 6909–6913, Aug. 1993.

* cited by examiner

Primary Examiner—Alexander Markoff
(74) Attorney, Agent, or Firm—Pennie & Edmonds LLP

(57) ABSTRACT

A docking station includes remotely actuated locking mechanisms for secure registration of reaction blocks, and provides for introduction of gases, liquids, and vacuum to the reaction blocks.

9 Claims, 8 Drawing Sheets

REACTION BLOCK DOCKING STATION

RELATED APPLICATIONS

This application is a continuation-in-part of application Ser. No. 08/718,106, filed Sep. 18, 1996 now abandoned, which is divisional of application Ser. No. 08/422,869, filed Apr. 17, 1995 now U.S. Pat. No. 5,609,826. U.S. Pat. No. 5,609,826 is incorporated herein by reference.

FIELD OF THE INVENTION

The present invention relates generally to apparatus used in combinatorial synthesis, and more particularly to a reaction block docking station.

BACKGROUND

The relationship between the structure and function of molecules is a fundamental issue in the study of biological and other chemistry-based systems. Structure-function relationships are important in understanding, for example, the functions of enzymes, cellular communication, and cellular control and feedback mechanisms. Certain macromolecules are known to interact with and bind to other molecules having a specific three-dimensional spatial and electronic distribution. Any macromolecule having such specificity can be considered a receptor, whether the macromolecule is an enzyme, a protein, a glycoprotein, an antibody, an oligonucleotide sequence of DNA, RNA, or the like. The various molecules to which receptors bind are known as ligands.

Pharmaceutical drug discovery is one type of research that relies on the study of structure-function relationships. Much contemporary drug discovery involves the discovery of ligands with desirable patterns of specificity for biologically important receptors. Thus, the time necessary to bring new drugs to market could be greatly reduced through the use of methods and apparatus that allow rapid generation and screening of large numbers of ligands.

A common way to generate such ligands is to synthesize libraries of ligands on solid phase resins. Techniques for solid phase synthesis of peptides are described, for example, in Atherton and Sheppard, *Solid Phase Peptide Synthesis: A Practical Approach*, IRL Press at Oxford University Press, Oxford, England, 1989. Techniques for solid phase synthesis of oligonucleotides are described in, for example, Gait, *Oligonucleotide Synthesis: A Practical Approach*, IRL Press at Oxford University Press, Oxford, England, 1984. Both of these references are incorporated herein by reference.

Since the introduction of solid phase synthesis methods for peptides, oligonucleotides and other polynucleotides, new methods employing solid phase strategies have been developed that are capable of generating thousands, and in some cases even millions, of individual peptide or nucleic acid polymers using automated or manual techniques. These synthesis strategies, which generate families or libraries of compounds, are generally referred to as "combinatorial chemistry" or "combinatorial synthesis" strategies.

To aid in the generation of combinatorial chemical libraries, scientific instruments have been produced that automatically perform many or all of the steps required to generate such libraries. An example of an automated combinatorial chemical library synthesizer is the Model 396 MPS fully automated multiple peptide synthesizer, manufactured by Advanced ChemTech, Inc. ("ACT") of Louisville, Ky.

The Model 396 MPS is capable of generating up to 96 different peptides (or other small molecules) in a single run. The syntheses occur simultaneously, with one amino acid being added to each growing polypeptide chain before addition of the next successive amino acid to any polypeptide chain. Thus, each growing polypeptide chain contains the same number of amino acid residues at the end of each synthesis cycle. The syntheses occur in an ACT proprietary plastic reaction block that has 96 reaction chambers.

Although the ACT Model 396 works for its intended purpose, it possesses several shortcomings. For example, since the ACT reaction blocks are machined from a single piece of plastic, they require extremely intricate machining and are quite expensive to manufacture. Moreover, should a portion of a block become damaged or contaminated in some way, the entire reaction block would have to be discarded; there is no way to replace individual portions of an ACT block. An additional drawback of the plastic ACT reaction blocks is that they cannot be efficiently heated or cooled to aid in chemical reactions that may require such heating or cooling.

Certain processes and chemistries require that the chemical reagents (which may be reactants, solvents, or reactants dissolved in solvents) be kept under an inert or anhydrous atmosphere to prevent reactive groups from reacting with molecular oxygen, water vapor, or other agents commonly found in air. Examples of atmosphere or moisture sensitive chemistries include peptide chemistry, nucleic acid chemistry, organometallic, heterocyclic, and other chemistries commonly used to construct combinatorial chemical libraries.

Although the ACT reaction block can maintain an inert atmosphere when locked in place on the work station of the Model 396 MPS, there is no way to maintain an inert atmosphere once an ACT reaction block is removed from the work station. Thus, the reaction block must remain docked at the work station during the entire synthesis cycle. Since many reactants require several hours to react, this represents significant down time for the Model 396 MPS, as it remains idle during the reaction period.

The ACT reaction block includes 96 reaction chambers; however, the compounds generated in the ACT reaction block cannot be transferred directly into a standard 96-well microtiter plate because the distance between the outlets of the reaction chambers is too great. When reactions are complete, the user must transfer the contents of the reaction chambers into an array of 96 flat bottom glass vials supported in a plastic frame. The user must then manually pipette fluid from the glass vials into a microtiter plate for further analysis.

U.S. Pat. Nos. 3,944,188 and 4,054,141 to Parker et al. disclose a concentrating vortexing shaker that can receive a thermally conductive vessel block. The vessel block of Parker et al. has a plurality of openings for receiving sample laboratory vessels; the vessel block also has passages through which a hearing or cooling liquid may be passed. After the vessel block of Parker et al. is mounted on the vortexing shaker, an air-tight cover may be attached to the block, forming a chamber over the vessels in the block. A vacuum may then be applied to the chamber.

Although the vortexing shaker and vessel block of Parker et al. may be useful to facilitate particular types of chemical reactions (and when only a small number of samples needs to be generated), the structures disclosed in Parker et al. possess many disadvantages that make them unsuitable for use in the efficient generation of chemical libraries. For example, a vacuum or inert atmosphere may be maintained in the vessel block of Parker et al. only when the vessel block is mounted on the vortexing shaker. Moreover, nothing can be added to the vessels of Parker et al. when the air-tight cover is attached to the vessel block.

To secure the vessel block of Parker et al. to the vortexing shaker, vacuum and cooling hoses from the vortexing shaker must be attached to the block manually, and the block itself must be secured to the shaker with a manually operated knob. Again, a common objective of combinatorial synthesis is to generate a very large number of compounds. The several manual operations required to use the vessel block and vortexing shaker of Parker et al. therefore make the use of these structures too inefficient and time consuming for use in the generation of very large chemical libraries.

In light of the deficiencies in the prior art, there remains a need in the art for an apparatus that allows for the fully automated and rapid generation of combinatorial chemical libraries.

SUMMARY

The preferred embodiments meet these needs by providing a reaction block docking station that uses remotely actuated locking mechanisms to quickly and automatically secure reaction blocks into the docking station. A preferred docking station allows the reaction blocks to be heated or cooled, provides for introduction of gases or liquids into the reaction blocks, and provides a vacuum source that can be used to remove liquids or gasses from the reaction blocks. A preferred docking station also allows reaction blocks to be removed from the docking station quickly, automatically, and without the leakage of liquids.

DETAILED DESCRIPTION

Figure 1:
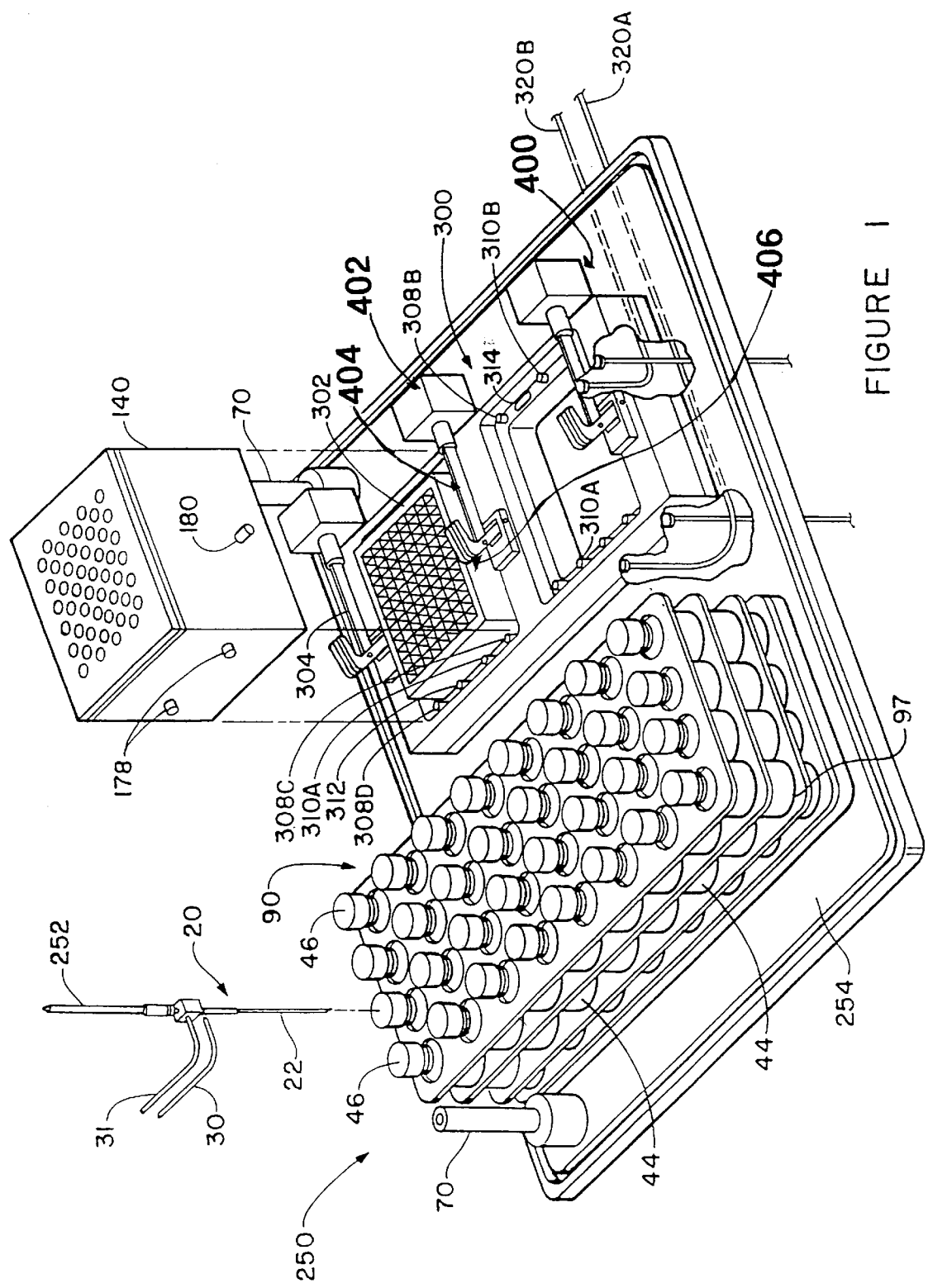
FIG. 1 is an isometric view of a pipetting work station that includes a preferred embodiment of a reaction block docking station.

The structure and function of the preferred embodiments can best be understood by reference to the drawings. The reader will note that the same reference numerals appear in multiple figures. Where this is the case, the numerals refer to the same or corresponding structure in those figures.

General Operation

FIG. 1 is an isometric view showing a portion of an automated pipetting work station 250 as may be used in a preferred embodiment. Automated pipetting work station 250 may be a TECAN 5032 automated pipetting work station (Manufactured by TECAN, AG, Feldbachstrasse 80, CH-8634 Hombrechtikon, Switzerland) with one or more pipetting arms 252. Pipetting arm 252 attaches to needle assembly 20. Needle assembly 20 may include a needle 22, a gas inlet port 30, and an electrical connection 31. Work station 250 may also include pipetting needle rinse stations 70.

A reagent container rack 90 may hold several containers 44 of reagents sealed from the outside air with septum seals 46. Rack 90 is preferably placed on the left side of work station deck 254. On the right side of work station deck 254 is a docking station 300 for receiving two reaction blocks 140. Each reaction block 140 preferably contains an array of 48 reaction chambers 110 (see, e.g., FIG. 2). A standard 96 well microtiter plate 302 may be mounted below reaction block 140 when product is to be removed from reaction chambers 110.

Reaction Block

Figure 2:
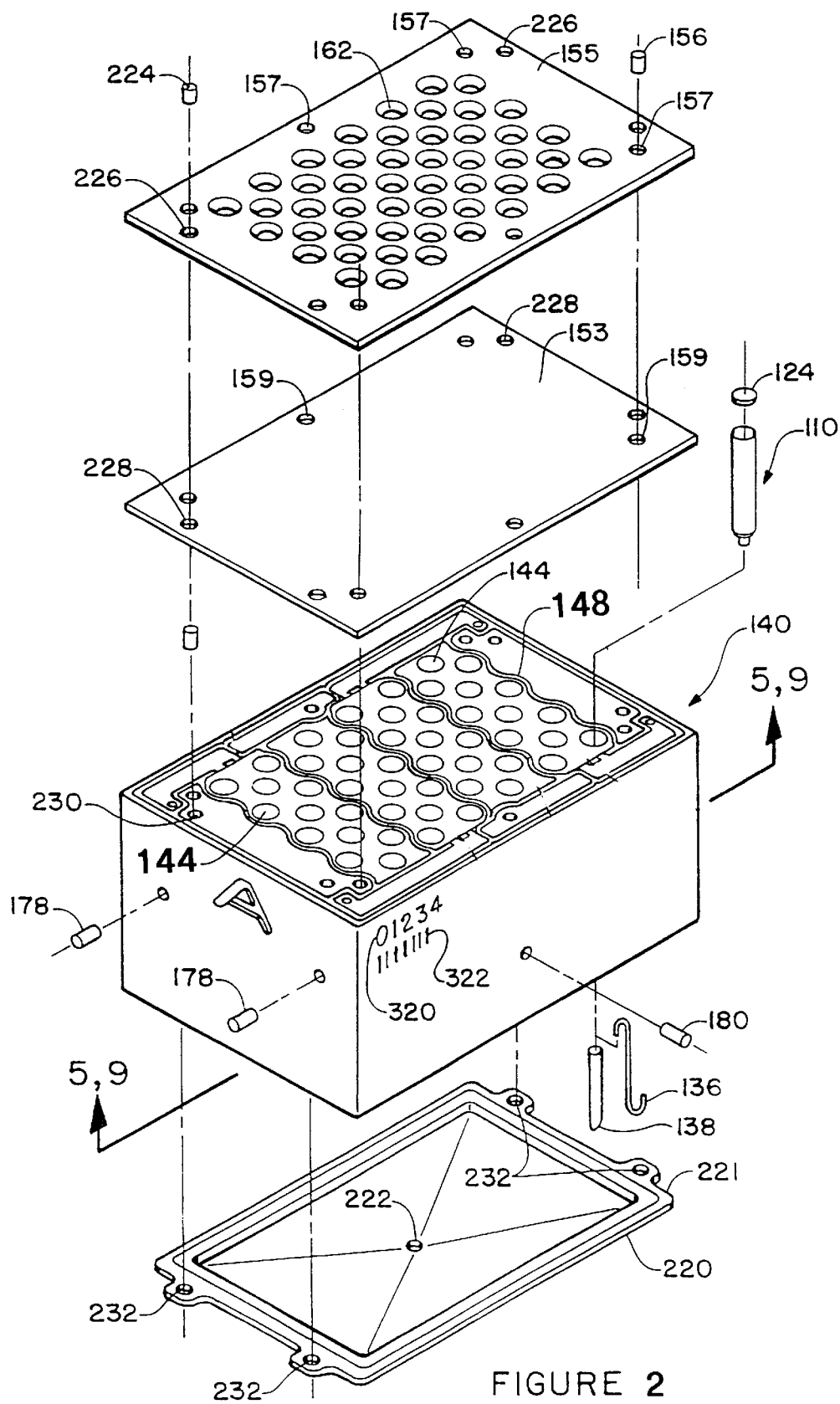
FIG. 2 is an exploded isometric view of a reaction block and its associated hardware according to a preferred embodiment.

Referring now to FIG. 2, an exploded isometric view of a reaction block 140 (and its associated hardware) according to a preferred embodiment is shown. Reaction block 140 is preferably machined out of 6061 aluminum and then anodized for additional corrosion protection. Reaction block 140 could also be hard coat anodized and then impregnated with teflon. Additionally, reaction block 140 could be machined or molded from any suitable metal, engineering plastics, filled plastics, crystalline plastics, ceramics, machinable ceramics, or any other material that can withstand the temperature, pressure, and chemical environment to which reaction block 140 will be exposed. If non-metallic materials are used, product reaction could be enhanced by the application of microwaves. If materials transparent to ultraviolet (UV) light are used, product could be cleaved from the synthesis support using UV light, and without the application of an acid or base.

Each reaction block 140 preferably holds 48 reaction chambers 110 that are mounted within openings 144. Reaction chamber 110 is preferably made of an injection molded or extruded polymer such as polypropylene, although polyethylene, teflon, glass, or any other inert material able to withstand the temperature, pressure, and chemical environment to which reaction chamber 110 is exposed could also be used. Reaction chamber 110 preferably also has an internal volume of approximately 2 ml.

The lower portion of reaction chamber 110 can receive a frit 124, which preferably supports a quantity of a synthesis support, such as solid phase resin (not shown). Frit 124 is preferably a 70 micron polyethylene frit, although other types of frits (such as sintered glass, sintered metals, and sintered ceramics) may be used, depending on the type of chemistry to be performed.

The lower portion of reaction chamber 110 is preferably connected to an S-shaped trap tube 136. The purpose of trap tube 136 is to prevent the loss of liquids from reaction chamber 110 (when reaction chamber 110 is not pressurized) by bringing the level of an outlet for liquid above the normal liquid level of reaction chamber 110. Trap tube 136 connects to a drain tube 138. As will be discussed below, drain tube 138 will be positioned so as to deposit liquid into a well of a standard 96-well microtiter plate.

Each end of reaction block 140 is preferably fitted with two pins 178 to facilitate handling by a robotic gripper (not shown). Each side of reaction block 140 is preferably fitted with one pin 180 to facilitate securing reaction block 140 onto docking station 300. Robotic manipulation of reaction block 140 makes automation of the entire synthesis process possible. For example, reagents could be introduced into reaction chambers 110 when reaction block 140 is locked onto docking station 300 of pipetting work station 250. Reaction block 140 could then be moved to a separate docking station 300, vortexing shaker table, heating or cooling chamber, or any other location or device (not shown) useful in synthesis or the collection of material.

In a preferred embodiment, two types of reaction blocks capable of mating directly with a 96 well microtiter plate are contemplated: the 48 reaction chamber 110 (and drain tube 138) positions of a first type of (or "A") block are offset from the 48 reaction chamber and drain tube positions of a second type of (or "B") block such that a type "A" and a type "B" block can fill every position in a standard 96 well microtiter plate. The ability to deposit material directly into a 96-well microtiter plate eliminates possible contamination and human error problems that are associated with the ACT reaction block discussed above.

Reaction block 140 may be color coded for ease of identification, may have identification numbers 320 machined into or printed on the sides, and may also have a bar code 322 printed on the side for identification by machine.

Top surfaces of reaction chambers 110 and raised sealing beads 148 are sealed by a sheet of septum material 153. Septum 153 is preferably manufactured from 1/10" thermoplastic rubber (TPR) sheet. Septum 153 is retained by a septum retainer plate 155, which is preferably fastened with six captive screw-type fasteners 156 that attach to openings 157. Fasteners 156 pass through openings 159 in septum 153, and screw into machined fastener openings 158.

Reaction block 140 may be sealed from underneath with a bottom seal 220. An o-ring or quad ring 221 (see FIG. 3) may be used to ensure a gas-tight seal. Bottom seal 220 may include a one-way valve 222 to allow pressure regulation. Bottom seal 220 is preferably fitted to reaction block 140 with screw-type fasteners 224. As can be seen in FIG. 2, fasteners 224 pass through openings 226 in plate 155, through openings 228 in septum 153, through openings 228 in reaction block 140, and into openings 232 in bottom seal 220.

Bottom seal 220 permits a desired atmosphere or pressure to be maintained within reaction block 140, allowing reaction block 140 to be moved from location to location (such as to a separate shaker table, not shown) without loss of such atmosphere or pressure. This can be especially useful in chemistries that require long periods of time for reactions to take place. In these situations, such reactions can take place away from the pipetting work station, allowing the pipetting work station to be used for other purposes.

In a preferred embodiment, septum retainer plate 155 is machined from 6061 aluminum, and then anodized. However, retainer plate 155 could also be machined or molded from engineering plastics, ceramics, or any other material that can withstand the temperature, pressure, and chemical environment to which retainer plate 155 will be exposed.

Plate 155 is also preferably machined with 48 openings 162 positionally matched with openings 144 of reaction block 140 (and thus with the openings of reaction chambers 110) to accurately control the compression of the septum 153 between the tops of reaction chambers 110, and plate 155.

Figure 3:
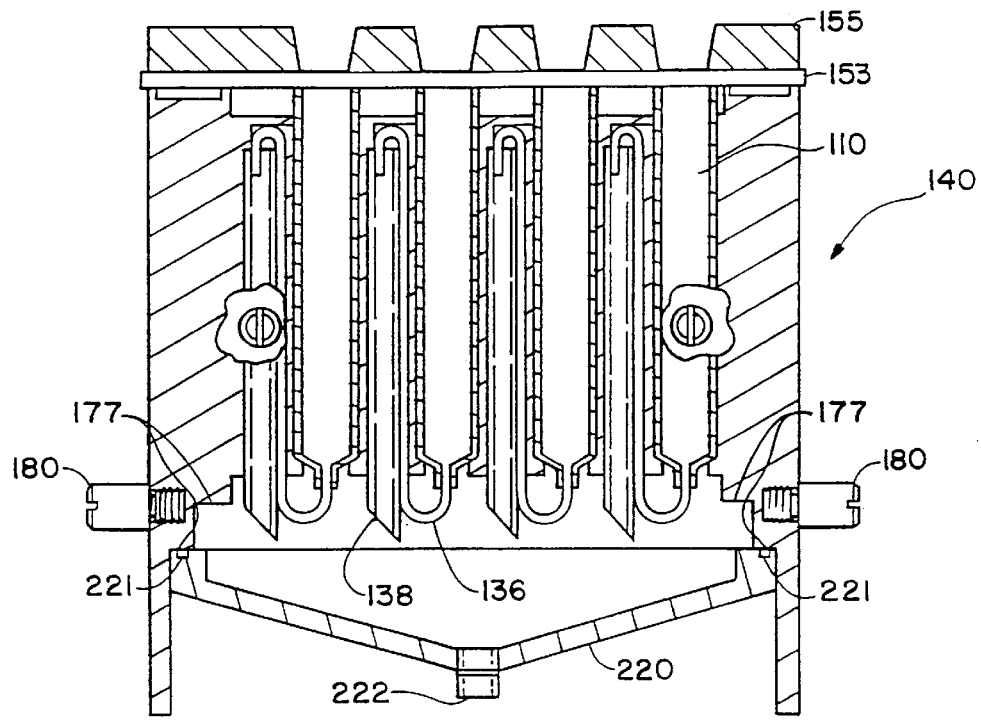
FIG. 3 is a side cross-sectional view of the reaction block shown in FIG. 2 including a removable bottom seal.
Figure 4:
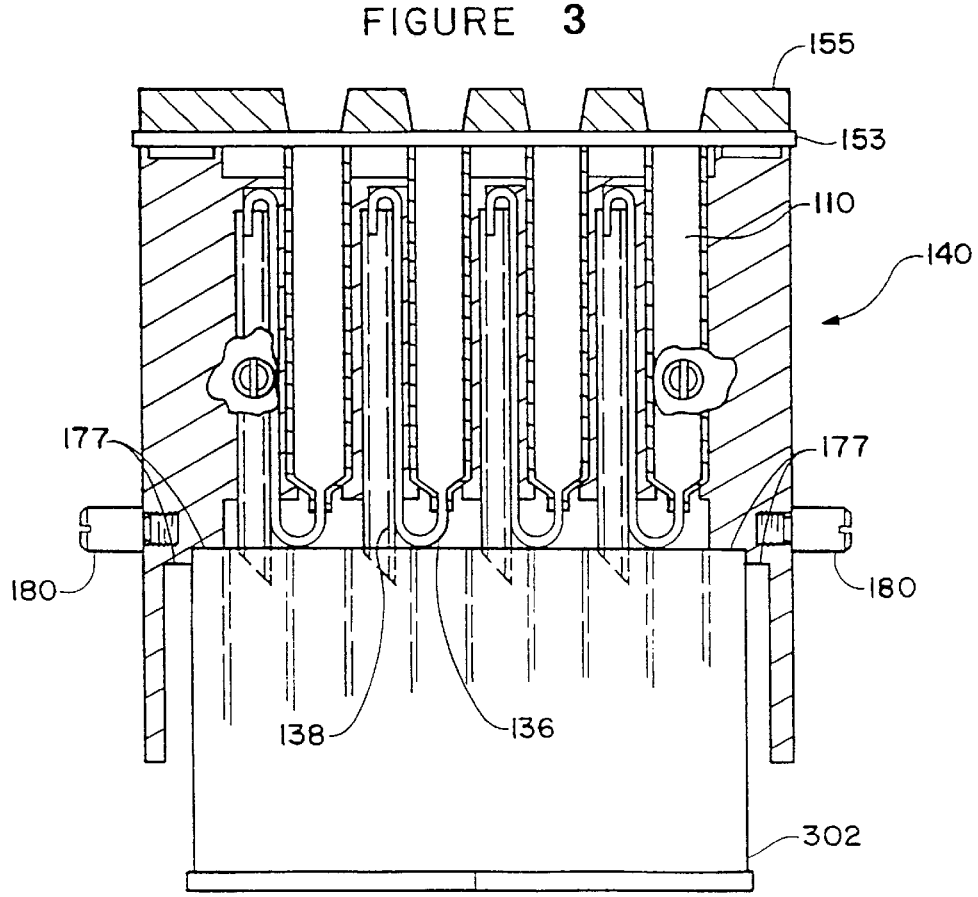
FIG. 4 is a side cross-sectional view of the reaction block shown in FIG. 2 including a microtiter plate.

Referring now to FIGS. 3 and 4, side cross-sectional views of reaction block 140 are shown. Steps 177 are machined into the bottom of reaction block 140 to allow reaction block 140 to mate directly with a standard 96-well microtiter plate 302. Steps 177 also allow mating and sealing with bottom seal 220.

Figure 5:
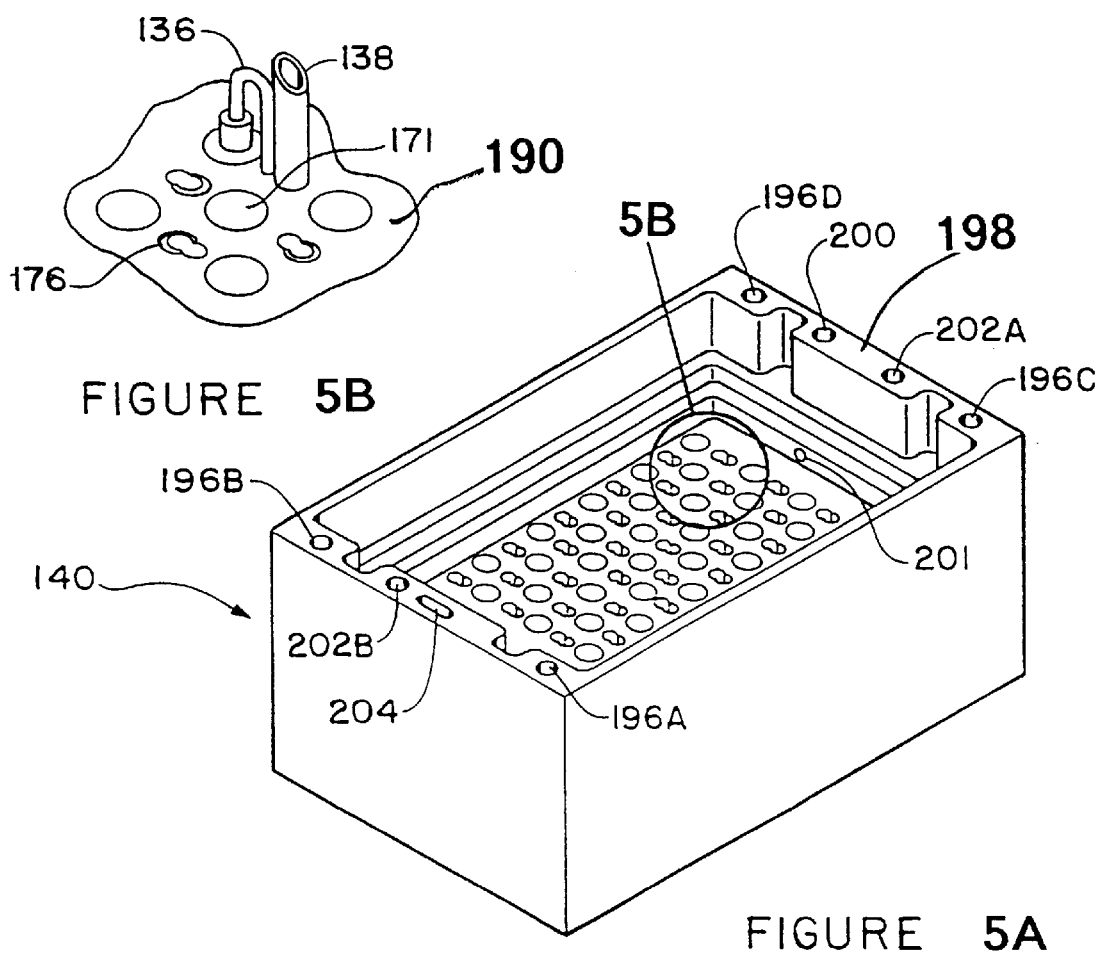
FIGS. 5A and 5B show bottom isometric views of the reaction block shown in FIG. 2.

Referring now to FIGS. 5A and 5B, isometric views of the underside of reaction block 140 are shown. The underside of reaction block 140 includes a generally planar surface 190 that includes a plurality of openings 171 and 176. Openings 176 accommodate drain tube 138 and s-shaped trap tube 136. The underside of reaction block 140 preferably also includes four gas ports 196A through 196D located on bottom surface 198.

Also included on bottom surface 198 is a gas inlet port 200 that connects to a gas outlet port 201 via a machined tunnel (not shown). This allows pressure on the underside of reaction block 140 to be independently controlled when it is sealed by bottom seal 220 (see FIGS. 2 and 3).

Bottom surface 198 also includes two ports 202A and 202B. The interior of reaction block 140 is preferably machined to include passages (not shown) in which a heating or cooling fluid (preferably a gas) can flow if desired. Gas can enter port 202A and exit through port 202B, or vice versa. If reaction block 140 is made of material having high thermal stability or thermal mass (such as 6061 aluminum), this arrangement allows reaction block 140 to be quickly and efficiently heated or cooled for chemistries that require such heating or cooling. Ports 196A–D, 200 and 202 may also serve as guide pin holes to position reaction block 140 properly on docking station 300 (see FIGS. 1, 6, and 7).

Finally, a bar magnet 204 may be mounted flush with surface 198. Bar magnet 204 serves to activate magnetic reed switch 314 mounted in docking station 300 (see FIGS. 1 and 6). As will be discussed below, one or more reed switches preferably prevent the operation of work station 250 unless one or more reaction blocks 140 are properly in place.

Docking Station

Figure 6:
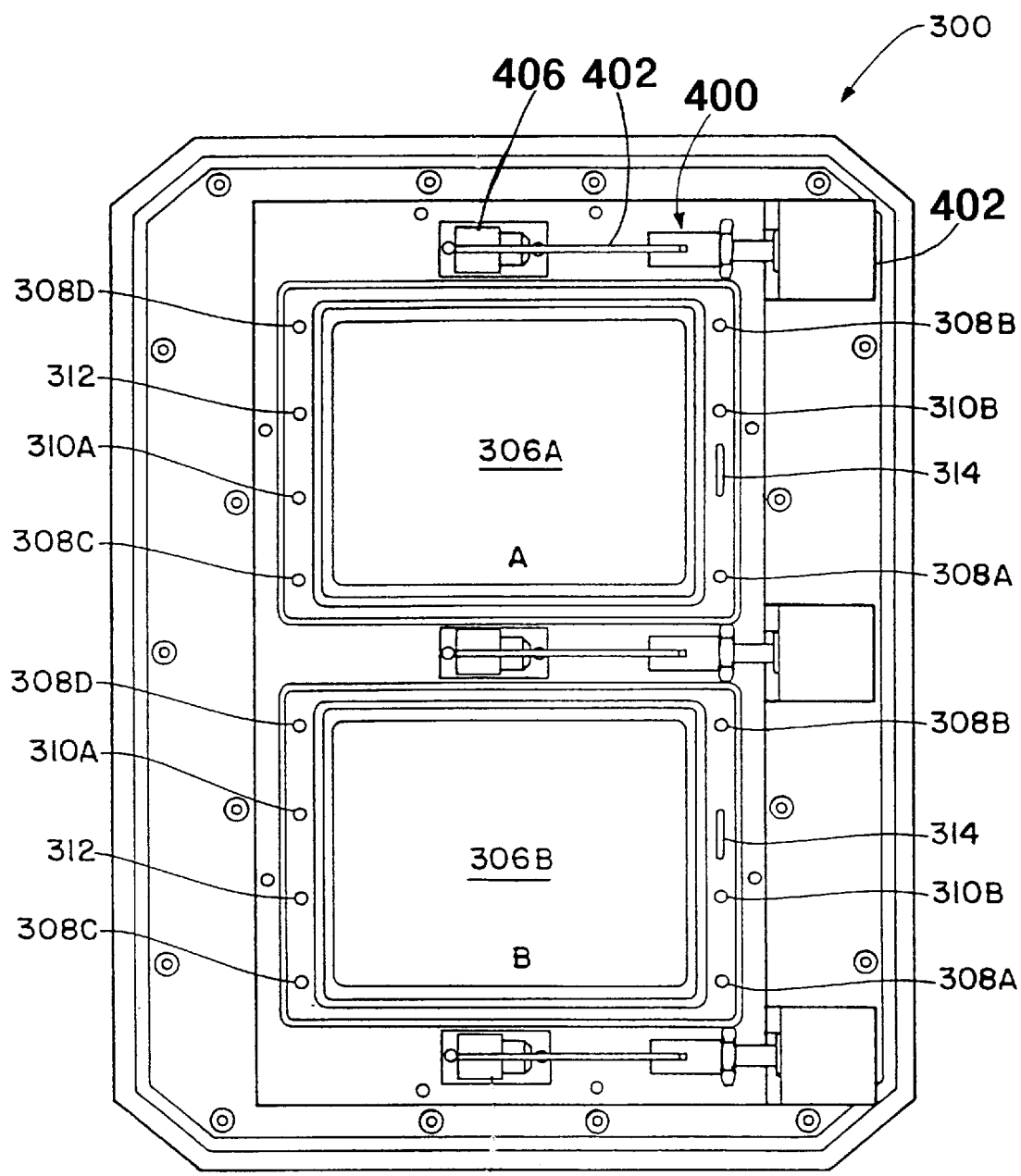
FIG. 6 is a top plan view of the docking station included in FIG. 1.

Referring now to FIGS. 1 and 6, a docking station 300 according to a preferred embodiment is shown. Docking station 300 preferably includes two stations, 306A and 306B, that include cavities for removably receiving reaction blocks 140 of Type "A" and Type "B", respectively, as discussed above. As is known to those skilled in the art, docking station 300 may also be fitted with the proper motor, gears, and other elements (not shown) necessary for docking station 300 to act as a vortexing shaker, and preferably as a vortexing shaker having a fixed displacement and variable speed.

Docking station 300 preferably includes a remotely actuated cam locking mechanism 400. Cam locking mechanism 400 preferably includes a pneumatic air cylinder 402, a linkage 404, and a cam lock 406. Air cylinder 402 can cause linkage 404 and cam lock 406 to be in an extended position or in a retracted position. When linkages 404 and cam locks 406 are in a retracted position, cam locks 406 can engage pins 180 in the sides of reaction blocks 140. When linkages 404 and cam locks 406 are in an extended position, cam locks 406 release pins 180. Remotely actuated cam locking mechanisms 400 therefore allow reaction blocks 140 to be secured to, and released from, stations 306 quickly and automatically. This permits the synthesis process to be fully automated, and allows a greater number of reaction blocks to use docking station 300 per unit time. This is especially important when it is desired to generate a large combinatorial chemical library relatively quickly.

Each station 306 preferably includes gas outlet connectors 308A through 308D that connect to ports 196A through 196D, respectively, in reaction block 140 (see FIG. 5A). Each station 306 also includes two coolant or heating fluid (i.e., gas or liquid) connectors 310A and 310B. Fluid may flow out of connector 310A and into connector 310B, or vice versa. In an alternative embodiment, connectors 310A and 310B may be electrical connectors that can be used to power a resistive heating element (not shown) within block 140.

FIG. 1 shows fluid lines 320A and 320B attached to connectors 310A and 310B, respectively. Although not shown in FIGS. 1, 6, and 7, independently controllable fluid lines attach to each connector shown in docking station 300. Connectors 310A and 310B connect to ports 202A and 202B, respectively in reaction block 140 (See FIG. 5A). A gas outlet connector 312 that connects to gas inlet port 200 of reaction block 140 is also included in each station 306.

Stations 306A and 306B each preferably also include a presence detector 314 that can detect the presence of a reaction block 140. In a preferred embodiment, presence detector 314 is a magnetic reed switch that senses the presence of magnet 204 on reaction block 140. In a preferred embodiment, station 306A, and more specifically the placement of port 310B, is arranged such that only an A-type reaction block 140 can be fully inserted and locked into position. Similarly, station 306B, and more specifically the placement of port 310B, is arranged such that only a B-type reaction block 140 can be fully inserted and locked into position. In an alternative embodiment, stations 306 and blocks 140 may be configured such that either an A-type or B-type reaction block may be placed in either station 306. In such an embodiment, presence detector 314 (and magnets 204) are preferably configured such that station 306 can determine if an inserted reaction block 140 is of the A-type or of the B-type.

Figure 7:
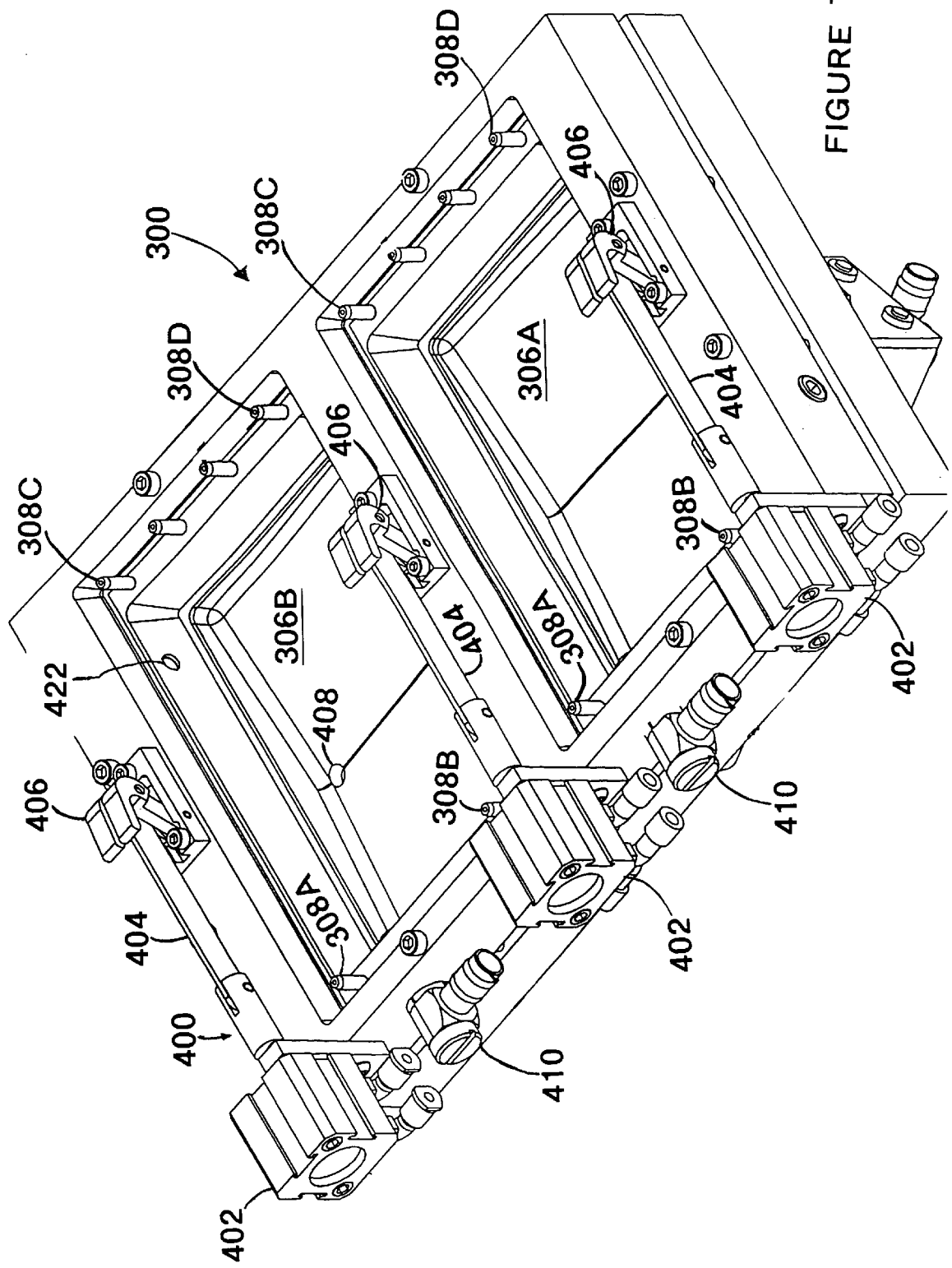
FIG. 7 is a top isometric view of a docking station according to an alternative embodiment.

FIG. 7 shows an alternative embodiment of docking station 300. The embodiment of FIG. 7 is preferably configured such that both A-type and B-type reaction blocks 140 may be inserted into either station 306A or 306B. A presence detector (not shown) is used to determine which type of reaction block is inserted into a particular station 306. Each station 306 also includes a presence detector 422 that can detect the presence of a microtiter plate. Presence detector 422 is preferably an optical sensor.

Docking station 300 of FIG. 7 includes a drain 408 at the bottom of each station 306. Each station 306 also includes a vacuum source connector 410. When applied to a vacuum source, vacuum source connector 410 (which is in vacuum communication with station 306) allows a vacuum to be applied to the bottom of reaction blocks 140 when they are secured to stations 306. Such vacuum application may be used to draw liquid from reaction chambers 110 via drain tubes 138 and trap tubes 136 (see, e.g., FIG. 4). Docking station 300 of FIG. 7 includes remotely actuated cam locking mechanisms 400 of the type discussed above with respect to FIG. 6.

Figure 8:
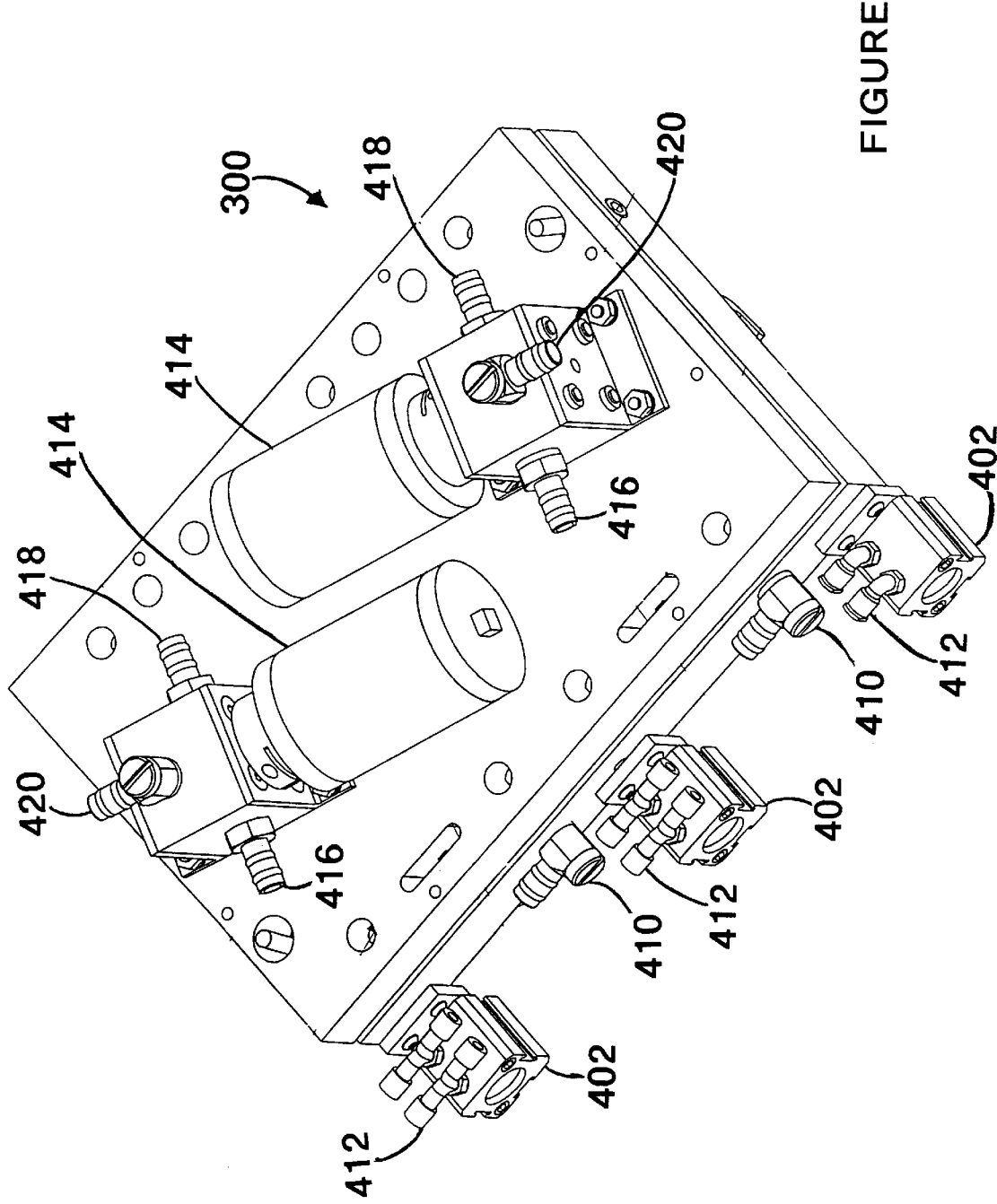
FIG. 8 is a bottom isometric view of the docking station shown in FIG. 7.

FIG. 8 is an isometric view of the underside of docking station 300 of FIG. 7. Pneumatic air cylinders 402 include compressed air line connectors 412. Connectors 412 are preferably connected to a source of compressed air (not shown) that can be used to operate remotely actuated pneumatic cylinder 402. Two pneumatic valves 414 are attached to the underside of docking station 300. Each valve 414 is positioned underneath a drain 408. A hose (not shown) is used to connect vacuum source connector 410 to connector 416 on valve 414. Connector 418 is connected to a vacuum source (not shown), and connector 420 is connected to a waste drain (not shown).

Figure 9:
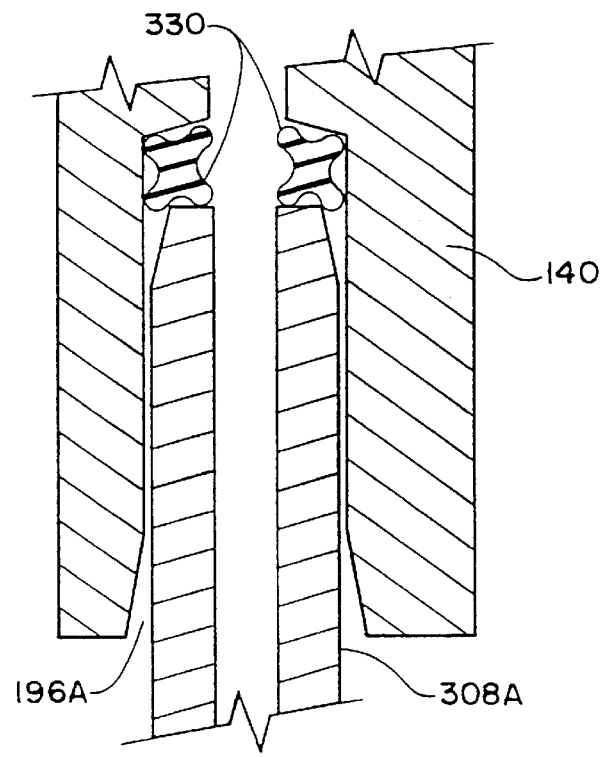
FIG. 9 is a cross sectional view of a connector in the docking stations shown in FIGS. 6 and 7, inserted into a port in the reaction block shown in FIG. 2.

Referring now to FIG. 9, a cross sectional view of a connector 308A inserted into port 196A of reaction block 140 is shown. Although only the interface between connector 308A and 196A will be discussed, it will be understood that similar interfaces are preferably included in other connections between reaction block 140 and docking station 300. In a preferred embodiment, connector 308A is inserted into port 196A. In this fashion, connector 308A acts as a guide pin to ensure proper alignment of reaction block 140 with station 306A. A gas-tight seal between connector 308A and port 196A is preferably provided by quad ring 330. A quad ring is preferred over a standard o-ring, because a quad ring has less tendency to adhere to surfaces when connector 308A is removed from port 196A.

Figures 10, 11:
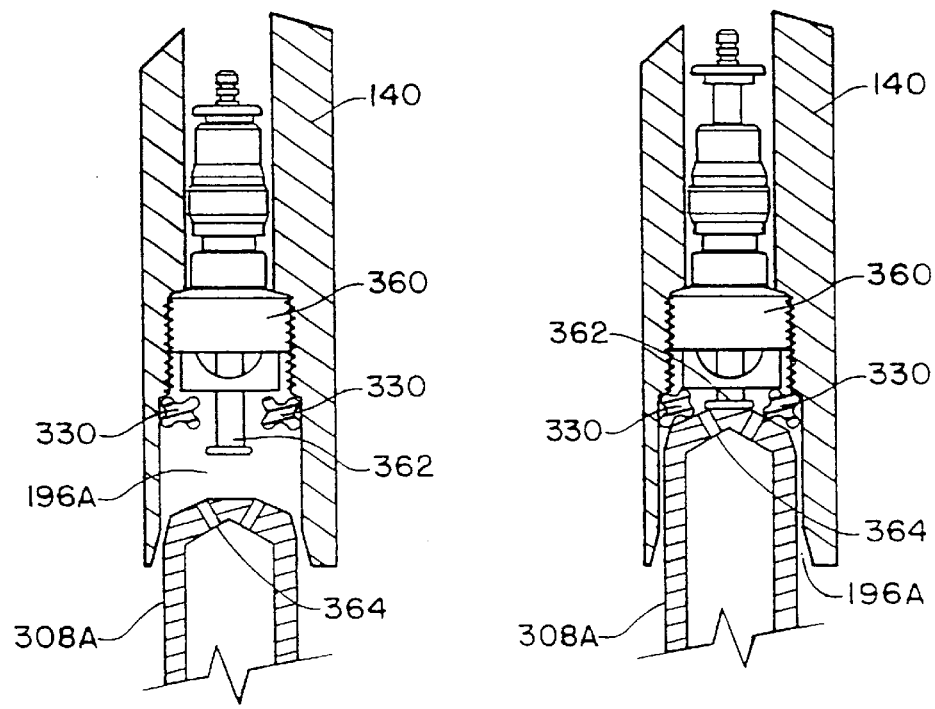
FIG. 10 is a cross sectional view of a connector in the docking stations shown in FIGS. 6 and 7, inserted into a port having a open valve in the reaction block shown in FIG. 2.
FIG. 11 is a cross sectional view of a connector in the docking stations shown in FIGS. 6 and 7, inserted into a port having a closed valve in the reaction block shown in FIG. 2.

FIGS. 10 and 11 show an alternative embodiment of port 196A. For operations in which inert or other atmosphere must be maintained, a normally closed valve, such as schraeder valve 360, may be placed in port 196A. Schraeder valve 360 may be replaced with a bi-directional elastomeric valve (not shown). In operation, connector 308A is inserted into port 196A and engages pin 362 of schraeder valve 360. Connector 308A also forms a seal against quad ring 330. Gas flows out of opening 364 and through schraeder valve 360. When connector 308A is removed from port 196A, pin 362 of schraeder valve 360 moves downward, creating a gas-tight seal.

EXAMPLE OF OPERATION

The many features of the preferred embodiments described above facilitate the relatively quick and efficient generation of chemical libraries. In the following discussion, a synthesis operation involving a type "A" reaction block 140 will be discussed. However, it will be understood that the following discussion will apply equally for a type "B" block as well.

In a typical operation, a synthesis support such as solid phase resin is deposited onto each frit 124 in reaction chambers 110. Reaction block 140 is then assembled as shown in FIG. 2. Bottom seal 220 may be mounted if reaction block 140 must be moved from place to place while maintaining a desired atmosphere or pressure.

Reaction block 140 may then be manually or robotically inserted into station 306A of docking station 300 on work station 250 (see FIGS. 1, 6, and 7). At this point, microtiter plate 302 is not located in station 306A. Remotely actuated locking mechanisms 400 (specifically cam locks 406) then grip pins 180, locking reaction block 140 into place. A type "B" reaction block may be simultaneously mounted in station 306B.

Pipetting work station 250 then operates under computer control to deliver the chosen combination of reagents into reaction chambers 110. Specifically, pipetting needle 22 (as controlled by pipetting arm 252) is used to transfer reagents from containers 44 into reaction chambers 110. The interior and exterior of pipetting needle 22 may be cleaned as necessary in rinse stations 70. At any time that reaction block 140 is mounted in station 306A, reaction block 140 may be heated or cooled, pressurized with inert gas, or vortexed as described above. When reaction block 140 is to be removed from station 306A, remotely actuated cam locking mechanisms 400 (and specifically cam locks 406) release pins 180. Reaction block 140 may then be robotically or manually removed from station 306A.

For reactions that take a considerable amount of time, reaction block 140 may be manually or robotically moved to another docking station 300, or to some other location while the reactions are taking place. After the syntheses of the desired products has been completed, the products may be cleaved from the synthesis supports using the appropriate reagents. These reagents may be applied at work station 250, or they may be applied robotically at some other location. If bottom seal 220 had been mounted, it is then removed, and reaction block 140 is mounted onto a microtiter plate 302 in station 306A. Reaction chambers 110 may then be pressurized, forcing the product out drain tubes 138 and into alternate wells of microtiter plate 302. Alternatively, a vacuum may be applied to the underside of reaction block 140. This vacuum pulls the product out of reaction chambers 110 via drain tubes 138 and trap tubes 136. Microtiter plate 302 is then moved to station 306B. A type "B" reaction block 140 is mounted on microtiter plate 302, and product is then deposited into the alternate empty wells of microtiter plate 302 as discussed above. Again, this process allows product to be deposited directly into the wells of a standard microtiter plate, without requiring an intermediate step.

The present invention has been described in terms of a referred embodiment. The invention, however, is not limited to the embodiment depicted and described. Rather, the scope of the invention is defined by the appended claims.

What is claimed is:

1. A docking station for receiving a reaction block, the docking station comprising:
    a platform including a cavity capable of removably receiving a first reaction block, said cavity comprising an inner portion capable of removably receiving a microtiter plate having a plurality of wells;
    a plurality of gas outlet connectors positioned within said cavity capable of coupling with the reaction block for providing gas to the reaction block;
    a reaction block presence detector positioned within said cavity to detect the presence of the reaction block in said cavity; and
    a locking device for securing the reaction block to said cavity.

2. A docking station as in claim 1, further comprising a heating or cooling fluid outlet connector positioned within said cavity capable of coupling with the reaction block for providing a heating or cooling fluid to the reaction block.

3. A docking station as in claim 1, wherein said detector is a reed switch.

4. A docking station as in claim 1, further comprising a second cavity capable of receiving a second reaction block.

5. A docking station as in claim 1, wherein said locking device comprises:
    a cam lock capable of engaging a pin extending from the reaction block; and
    a linkage pivotably coupled to said cam.

6. A docking station as in claim 4, wherein said cavity is capable of receiving the first reaction block that is of a first type and said second cavity is capable of receiving the second reaction block that is of a second type.

7. A docking station as in claim 1, said cavity further comprising
    an annular portion capable of mating with the reaction block, said annular portion comprising said gas outlet connectors.

8. A docking station as in claim 7, wherein said cavity is capable of individually receiving a first type of reaction block and a second type of reaction block, the first type of reaction block for depositing samples into a first set of microtiter plate wells and the second type of reaction block for depositing samples into a second set of microtiter plate wells.

9. A docking station as in claim 8, wherein said reaction block presence detector distinguishes between the first type of reaction block and the second type of reaction block.

* * * * *